(12) United States Patent
Rosevear et al.

(10) Patent No.: US 7,695,726 B2
(45) Date of Patent: Apr. 13, 2010

(54) PIGMENTED COSMETIC COMPOSITION EXHIBITING RADIANCE WITH SOFT FOCUS

(75) Inventors: Jeffrey William Rosevear, Shelton, CT (US); Brian John Dobkowski, Milford, CT (US); Prem Chandar, Closter, NJ (US); Marc Nicolaas Gerard De Mul, Hoboken, NJ (US); Jack Polonka, Peekskill, NY (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 1741 days.

(21) Appl. No.: 10/841,867

(22) Filed: May 7, 2004

(65) Prior Publication Data

US 2005/0163730 A1    Jul. 28, 2005

(51) Int. Cl.
*A61K 8/02* (2006.01)
(52) U.S. Cl. .................................................... 424/401
(58) Field of Classification Search ........................ None
See application file for complete search history.

(56) References Cited

U.S. PATENT DOCUMENTS

| | | |
|---|---|---|
| 5,032,390 A | 7/1991 | Iwaya et al. |
| 5,266,321 A | 11/1993 | Shukuzaki et al. |
| 5,427,771 A | 6/1995 | Grollier et al. |
| 5,443,759 A | 8/1995 | Dahms |
| 5,486,354 A | 1/1996 | Defossez et al. |
| 5,505,935 A | 4/1996 | Guerrero et al. |
| 5,560,917 A | 10/1996 | Cohen et al. |
| 5,587,148 A | 12/1996 | Mitchell et al. |
| 5,599,533 A | 2/1997 | Stepniewski et al. |
| 5,618,522 A | 4/1997 | Kaleta et al. |
| 5,688,831 A | 11/1997 | El-Nokaly et al. |
| 5,690,916 A | 11/1997 | Kimura et al. |
| 5,879,718 A | 3/1999 | Sebillote-Arnaud |
| 5,919,468 A | 7/1999 | Bara |
| 5,972,359 A | 10/1999 | Sine et al. |
| 5,989,570 A | 11/1999 | Lion et al. |
| 5,997,887 A | 12/1999 | Ha et al. |
| 5,997,890 A | 12/1999 | Sine et al. |
| 6,001,377 A | 12/1999 | SaNogueira, Jr. et al. |
| 6,024,942 A | 2/2000 | Tanner et al. |
| 6,024,944 A | 2/2000 | Hansenne |
| 6,174,533 B1 | 1/2001 | SaNogueira, Jr. et al. |
| 6,187,298 B1 | 2/2001 | Kurz et al. |
| 6,207,175 B1 | 3/2001 | Lebreton |
| 6,261,542 B1 | 7/2001 | Bara et al. |
| 6,306,409 B1 | 10/2001 | Ogawa et al. |
| 6,358,495 B1 | 3/2002 | Nishihama et al. |
| 6,432,535 B1 | 8/2002 | Noguchi et al. |
| 6,488,756 B1 | 12/2002 | Schoen et al. |
| 6,524,598 B2 | 2/2003 | Sunkel et al. |
| 6,747,115 B2 * | 6/2004 | Sakuta .................. 528/31 |
| 2002/0028223 A1 * | 3/2002 | Vatter et al. ............. 424/401 |
| 2002/0155076 A1 | 10/2002 | Lanzendorfer et al. |
| 2003/0171479 A1 | 9/2003 | Lennon |
| 2004/0120908 A1 * | 6/2004 | Cohen et al. .............. 424/63 |
| 2004/0228815 A1 | 11/2004 | L'Alloret |

FOREIGN PATENT DOCUMENTS

| | | |
|---|---|---|
| EP | 1 468 670 A1 | 3/2004 |
| FR | 2 834 450 | 1/2002 |
| JP | 61-194009 | 8/1986 |
| JP | 08-295620 | 11/1996 |
| WO | 03/022236 A1 | 3/2003 |
| WO | 03/099253 A1 | 12/2003 |
| WO | 2004/039338 A1 | 5/2004 |

* cited by examiner

*Primary Examiner*—Robert A Wax
*Assistant Examiner*—Melissa S Mercier
(74) *Attorney, Agent, or Firm*—Milton L. Honig

(57) ABSTRACT

A cosmetic composition is provided which includes a crosslinked silicone elastomer, a zinc oxide or zirconium oxide of average particle size less than 300 nm and a light reflecting inorganic material of platelet shaped particles having an average particle size of about 10,000 to about 30,000 nm, in a cosmetically acceptable carrier system. The composition achieves soft focus and radiance properties which improve the appearance of skin. Good coverage over imperfections such as pores and uneven skin tone is achieved while retaining a natural skin appearance.

23 Claims, No Drawings

PIGMENTED COSMETIC COMPOSITION EXHIBITING RADIANCE WITH SOFT FOCUS

BACKGROUND OF THE INVENTION

1. Field of the Invention

The invention relates to compositions for improving the appearance of skin, particularly to provide good coverage over imperfections such as pores and uneven skin tone, while retaining a natural skin appearance.

2. The Related Art

A matte effect is desired for users of color cosmetics. The matte finish overcomes the shiny effect engendered by greasy skin, particularly under hot and humid conditions. Absorbent fillers such as talc, silica, kaolin and other inorganic particulates have been used to achieve the effect by their optical properties.

Imperfect skin can be hidden in two ways through manipulation of light transmission. In the first, components of the color cosmetic may simply reflect light back toward the source. An alternative approach is referred to as achieving a soft focus effect. Here the incoming light is distorted by scattering (lensing). Components of the color cosmetic in this mechanism operate as lenses to bend and twist light into a variety of directions.

While it is desirable to hide imperfect skin through a matte effect, there is also a desire to achieve a healthy skin radiance. A cosmetic covering that is too opaque hides the skin under a paint-like coating. Imperfections are hidden but there is no radiance. Where light transmission is insufficiently hindered, the opposite occurs. Here the glow may be healthy but aesthetically displeasing skin topography and color may now be apparent.

U.S. Pat. No. 5,997,890 (Sine et al.), U.S. Pat. No. 5,972,359 (Sine et al.), and U.S. Pat. No. 6,174,533 B1 (SaNogueira, Jr.) are all directed to topical compositions to provide good coverage of skin imperfections. The solution proposed by these documents is the use of a metal oxide with a refractive index of at least about 2 and a neat primary particle size of from about 100 to about 300 nm. Preferred particulates are titanium dioxide, zirconium oxide and zinc oxide.

Silicone gelling agents such as crosslinked organopolysiloxane elastomers because of their excellent skinfeel properties have been found useful in make-up compositions. For instance, U.S. Pat. No. 5,266,321 (Shukuzaki et al.) discloses an oily make-up composition comprised of a silicone gel crosslinked elastomer, titanium dioxide, mica and iron oxides. Japanese patent application 61-194009 (Harashima) describes a make-up composition comprising a cured organopolysiloxane elastomer powder and pigments which may be selected from talc, titanium dioxide, zinc oxide and iron oxides.

A challenge which has not been fully met by the known art is delivery of a composition with appropriate optics to achieve both soft focus and radiance properties in a system that still provides excellent skinfeel.

SUMMARY OF THE INVENTION

A cosmetic composition is provided which includes:
(i) a crosslinked silicone elastomer;
(ii) a zinc oxide or zirconium oxide of average particle size less than 300 nm;
(iii) a light reflecting inorganic material of platelet shaped particles having an average particle size of about 10,000 to about 30,000 nm; and
(iv) a cosmetically acceptable carrier system.

DETAILED DESCRIPTION OF THE INVENTION

Now it has been observed that a soft focus effect with radiance can be obtained by a combination of fine particle sized zinc oxide or zirconium oxide suspended with a crosslinked silicone elastomer. The zinc or zirconium oxide must have an average particle size less than 300 nm. Absent the elastomer or the zinc or zirconium oxide, there would be insufficient soft focus effect. The oxide alone is inefficient because of excessive loss of reflectance/radiance.

Crosslinked Silicone Elastomer

A component of the present invention is a crosslinked silicone (organopolysiloxane) elastomer. No specific restriction exists as to the type of curable organopolysiloxane composition that can serve as starting material for the crosslinked silicone elastomer. Examples in this respect are addition reaction-curing organopolysiloxane compositions which cure under platinum metal catalysis by the addition reaction between SiH-containing diorganopolysiloxane and organopolysiloxane having silicon-bonded vinyl groups; condensation-curing organopolysiloxane compositions which cure in the presence of an organotin compound by a dehydrogenation reaction between hydroxyl terminated diorganopolysiloxane and SiH-containing diorganopolysiloxane; condensation-curing organopolysiloxane compositions which cure in the presence of an organotin compound or a titanate ester, by a condensation reaction between an hydroxyl terminated diorganopolysiloxane and a hydrolyzable organosilane (this condensation reaction is exemplified by dehydration, alcohol-liberating, oxime-liberating, amine-liberating, amide-liberating, carboxyl-liberating, and ketone-liberating reactions); peroxide-curing organopolysiloxane compositions which thermally cure in the presence of an organoperoxide catalyst; and organopolysiloxane compositions which are cured by high-energy radiation, such as by gamma-rays, ultraviolet radiation, or electron beams.

Addition reaction-curing organopolysiloxane compositions are preferred for their rapid curing rates and excellent uniformity of curing. A particularly preferred addition reaction-curing organopolysiloxane composition is prepared from:

(A) an organopolysiloxane having at least 2 lower alkenyl groups in each molecule;
(B) an organopolysiloxane having at least 2 silicon-bonded hydrogen atoms in each molecule; and
(C) a platinum-type catalyst.

The crosslinked siloxane elastomer of the present invention may either be an emulsifying or non-emulsifying crosslinked organopolysiloxane elastomer or combinations thereof. The term "non-emulsifying," as used herein, defines crosslinked organopolysiloxane elastomer from which polyoxyalkylene units are absent. The term "emulsifying," as used herein, means crosslinked organopolysiloxane elastomer having at least one polyoxyalkylene (e.g., polyoxyethylene or polyoxypropylene) unit.

Particularly useful emulsifying elastomers are polyoxyalkylene-modified elastomers formed from divinyl compounds, particularly siloxane polymers with at least two free vinyl groups, reacting with Si—H linkages on a polysiloxane backbone. Preferably, the elastomers are dimethyl polysiloxanes crosslinked by Si—H sites on a molecularly spherical MQ resin.

Preferred silicone elastomers are organopolysiloxane compositions available under the INCI names of dimethicone/vinyl dimethicone crosspolymer, dimethicone crosspolymer and Polysilicone-11. Ordinarily these materials are provided as a 1-30% crosslinked silicone elastomer dissolved or suspended in a dimethicone fluid (usually cyclomethicone). For purposes of definition "crosslinked silicone elastomer" refers to the elastomer alone rather than the total commercial compositions which also include a solvent (eg dimethicone) carrier.

Dimethicone/vinyl dimethicone crosspolymers and dimethicone crosspolymers are available from a variety of suppliers including Dow Corning (9040, 9041, 9045, 9506 and 9509), General Electric (SFE 839), Shin Etsu (KSG-15, 16, 18 [dimethicone/phenyl vinyl dimethicone crosspolymer]), and Grant Industries (Gransil™ line of materials), and lauryl dimethicone/vinyl dimethicone crosspolymers supplied by Shin Etsu (e.g, KSG-31, KSG-32, KSG-41, KSG-42, KSG-43, and KSG-44).

Other suitable commercially available silicone elastomer powders include vinyl dimethicone/methicone silesquioxane crosspolymers from Shin-Etsu sold as KSP-100, KSP-101, KSP-102, KSP-103, KSP-104, KSP-105, and hybrid silicone powders that contain a fluoroalkyl group or a phenyl group sold by Shin-Etsu as respectively KSP-200 and KSP-300.

The crosslinked silicone elastomers of the present invention may range in concentration from about 0.01 to about 30%, preferably from about 0.1 to about 10%, optimally from about 0.5 to about 2% by weight of the cosmetic composition. These weight values exclude any solvent such as cyclomethicone found in commercial "elastomer" silicones such as the Dow Corning products 9040 and 9045. For instance, the amount of crosslinked silicone elastomer in 9040 and 9045 is between 12 and 13% by weight.

Most preferred as the silicone elastomer is 9045 which has a D5 cyclomethicone swelled elastomer particle size (based on volume and calculated as spherical particles) which averages about 38 micron, and may range from about 25 to about 55 micron.

Micronized Zinc or Zirconium Oxide

A second important component of the present invention is that of a micronized zinc oxide or zirconium oxide having average (number) particle sizes less than 300 nm, preferably less than 200 nm, more preferably less than 100 nm and optimally less than 85 nm. Generally the particle sizes can range from about 0.01 to about 280 nm, more preferably from about 1 to about 200 nm, even more preferably from 10 to 95 nm, and optimally from 25 to 75 nm.

Average particle size of the oxide assumes a spherical shape and is defined as the diameter of the particle averaged over many particles. The average value is a number average. For spherical particles such as the zinc oxide, laser light scattering is utilized to determine the individual sizes of the particles and generate a particle size distribution plot. Based upon the distribution plot, the average particle size can be determined. In more mathematical terms, the average particle size is a diameter converted from the meso-pore specific surface area determined by the t-plot method (particle size converted excluding the specific surface area of micro pores of less than 20 Angstrom). In detail, the average particle size D, assuming the particle as spherical form, can be obtained by the following equation: $D=6/pS$, where S ($m^2/g$) represents a meso-pore specific surface area and p($g/cm^3$) is the density.

The amount of zinc oxide or zirconium oxide may range from about 0.1 to about 20%, preferably from about 0.5 to about 10%, optimally from about 1 to about 5% by weight of the cosmetic composition.

Since zinc or zirconium oxide particles are applied to skin, it is desirable that they be free of toxic trace metal contaminants. A particularly preferred zinc oxide has trace concentrations of lead (less than 20 ppm), arsenic (less than 3 ppm), cadmium (less than 15 ppm) and mercury (less than 1 ppm). This material is commercially available from BASF Corporation under the trademark of Z-Cote HP1. These particles are best delivered to the formula as a pre-mix of 5-80% weight by weight suspended in an organic ester base.

Zinc oxide or zirconium oxide particles of the present invention advantageously but not necessarily are substantially spherical in shape. The refractive index of these particles may preferably range from about 1.8 to about 2.3. Measurement of refractive index can be performed according to a method described in J. A. Dean, Ed., Lange's Handbook of Chemistry, $14^{th}$ Ed., McGraw Hill, New York 1992, Section 9, Refractometry, incorporated herein by reference.

Light Reflecting Platelet Particles

A third important component of compositions according to the present invention is that of light reflecting platelet shaped particles. These particles will have an average particle size $D_{50}$ ranging from about 10,000 to about 30,000 nm. For plate-like materials the average particle size is a number average value. The platelets are assumed to have a circular shape with the diameter of the circular surface averaged over many particles. The thickness of the plate-like particles is considered to be a separate parameter. For instance, the platelets can have an average particle size of 35,000 nm and an average thickness of 400 nm. For purposes herein, thickness is considered to range from about 100 to about 600 nm. Laser light scattering can be utilized for measurement except that light scattered data has to be mathematically corrected from the spherical to the non-spherical shape. Optical and electron microscopy may be used to determine average particle size. Thickness is normally only determined via optical or electron microscopy.

The refractive index of these particles is preferred to be at least about 1.8, generally from about 1.9 to about 4, more preferably from about 2 to about 3, optimally between about 2.5 and 2.8.

Illustrative but not limiting examples of light reflecting particles are bismuth oxychloride (single crystal platelets) and titanium dioxide coated mica. Suitable bismuth oxychloride crystals are available from EM Industries, Inc. under the trademarks Biron® NLY-L-2X CO and Biron® Silver CO (wherein the platelets are dispersed in castor oil); Biron® Liquid Silver (wherein the particles are dispersed in a stearate ester); and Nailsyn® IGO, Nailsyn® II C2X and Nailsyn® II Platinum 25 (wherein the platelets are dispersed in nitrocellulose). Most preferred is a system where bismuth oxychloride is dispersed in a $C_2$-$C_{40}$ alkyl ester such as in Biron® Liquid Silver.

Among the suitable titanium dioxide coated mica platelets are materials available from EM Industries, Inc. These include Timiron® MP-10 (particle size range 10,000-30,000 nm), Timiron® MP-14 (particle size range 5,000-30,000 nm), Timiron® MP-30 (particle size range 2,000-20,000 nm), Timiron® MP-101 (particle size range 5,000-45,000 nm), Timiron® MP-111 (particle size range 5,000-40,000 nm), Timiron® MP-1001 (particle size range 5,000-20,000 nm), Timiron® MP-155 (particle size range 10,000-40,000 nm), Timiron® MP-175 (particle size range 10,000-40,000), Timiron® MP-115 (particle size range 10,000-40,000 nm), and Timiron® MP-127 (particle size range 10,000-40,000 nm). Most preferred is Timiron® MP-111. The weight ratio of titanium dioxide coating to the mica platelet may range from about 1:10 to about 5:1, preferably from about 1:1 to about 1:6, more preferably from about 1:3 to about 1:4 by weight. Advantageously the preferred compositions will generally be substantially free of titanium dioxide outside of that required for coating mica.

Suitable coatings for mica other than titanium dioxide may also achieve the appropriate optical properties required for the present invention. These types of coated micas must also meet the refractive index of at least about 1.8. Other coatings include silica on the mica platelets.

The amount of the light reflecting platelet shaped particles may range from about 0.1 to about 5%, preferably from about 0.5 to about 3%, more preferably from about 0.8 to about 2%, optimally from about 1 to about 1.5% by weight of the composition.

Advantageously the weight ratio of zinc oxide and zirconium oxide to light reflecting platelet shaped particles may range from about 4:1 to about 1:1, preferably from about 3:1 to about 1.5:1, optimally about 2:1 by weight. In a preferred but not limiting example, the amount of silicone elastomer and oxide particles relative to the light reflective platelet shaped particles may be present in a ratio from about 10:1 to about 1:1, preferably from about 6:1 to about 1:1, more preferably from about 5:1 to about 3:1, optimally about 4:1 by weight.

Advantageously compositions of the present invention will have a Reflectance Intensity as measured at a 30° angle ranging from 140 to 170 thousand Watt-nm/cm$^2$. Light Transmission Intensity advantageously ranges from 4 to 7 million Watt-nm/cm$^2$ at an angle of 0°; a Transmission Intensity ranging from 1 to 2 million Watt-nm/cm$^2$ at a 10° angle; a Transmission Intensity ranging from 120 to 140 thousand Watt-nm/cm$^2$ at a 30° angle; a Transmission Intensity ranging from 60 to 80 thousand Watt-nm/cm$^2$ at a 40° angle; and a Transmission Intensity ranging from 40 to 60 thousand Watt-nm/cm$^2$ at a 50° angle.

Optional Particles

Advantageously compositions of the present invention may include a non-coated mica. These mica particles can also be platelets but of thinner and smaller particle size than the coated micas mentioned above. Particularly preferred is Satin Mica, available from Merck-Rona. These are useful to remove any excessive glitter imparted by the light scattering platelets. Advantageously the particle size of the non-coated mica is no higher than 15,000 nm and an average (volume) particle size ranging from 1,000 to 10,000 nm, preferably from 5,000 to 8,000 nm.

The amount of the non-coated mica may range from about 0.05 to about 2%, preferably from about 0.1 to about 1.5%, optimally from about 0.4 to about 0.8% by weight of the composition.

Advantageously present may also be water-insoluble organic material in the form of polymeric porous spherical particles. By the term "porous" is meant an open or closed cell structure. Preferably the particles are not hollow beads. Average particle size may range from about 0.1 to about 100, preferably from about 1 to about 50, more preferably greater than 5 and especially from 5 to about 15, optimally from about 6 to about 10 μm. Organic polymers or copolymers are the preferred materials and can be formed from monomers including the acid, salt or ester forms of acrylic acid and methacrylic acid, methylacrylate, ethylacrylate, ethylene, propylene, vinylidene chloride, acrylonitrile, maleic acid, vinyl pyrrolidone, styrene, butadiene and mixtures thereof. The polymers are especially useful in cross-linked form. Cells of the porous articles may be filled by a gas which can be air, nitrogen or a hydrocarbon. Oil Absorbance (castor oil) is a measure of porosity and in the preferred but not limiting embodiment may range from about 90 to about 500, preferably from about 100 to about 200, optimally from about 120 to about 180 ml/100 grams. Density of the particles in the preferred but not limiting embodiment may range from about 0.08 to 0.55, preferably from about 0.15 to 0.48 g/cm$^3$.

Illustrative porous polymers include polymethylmethacrylate and cross-linked polystyrene. Most preferred is polymethyl methacrylate available as Ganzpearl® GMP 820 available from Presperse, Inc., Piscataway, N.J., known also by its INCI name of Methyl Methacrylate Crosspolymer.

Amounts of the water-insoluble polymeric porous particles may range from about 0.01 to about 10%, preferably from about 0.1 to about 5%, optimally from about 0.3 to about 2% by weight of the composition.

Carrier System and Optional Components

Advantageously present will be an associative polymer. Representative polymers which may be suitable for the present invention are listed in the Table below.

| Supplier | Name | INCI Name |
|---|---|---|
| Akzo Nobel | Elfacos T 212 | PPG-14 Palmeth-60 Hexyl Dicarbamate |
| Ciba | Salcare SC96 | Polyquaternium 37 and Propylene Glycol Dicaprate Dicaprylate and PPG-1 Trideceth-6 |
| Clariant | Aristoflex AVC | Ammonium Acryloyldimethyltaurate/VP Copolymer |
| Clariant | Aristoflex HMB | Ammonium Acryloyldimethyltaurate/Beheneth-25 Methacrylate Crosspolymer |
| Clariant | Aristoflex PEA | Polypropylene Terephthalate |
| Clariant | Hostacerin AMP5 | Ammonium Polyacryloyldimethyl Taurate |
| Hercules | Natrosol Plus CS | Cetyl Hydroxyethylcellulose |
| Hercules | PolySurf | Cetyl Hydroxyethylcellulose |
| National Starch | Structure 2001 | Acrylates/Steareth-20 Itaconate Copolymer |
| National Starch | Structure 3001 | Acrylates/Ceteth-20 Itaconate Copolymer |
| Noveon | Pemulen (various) | Acrylates/C10-30 Alkyl Acrylate Crosspolymer |
| RITA | Viscolam SMC 20 | Sodium Acrylate/Sodium Acryloyldimethyl Taurate Copolymer and C13-C14 Isoparaffin and Laureth-8 |
| SEPPIC | Sepigel 305 | Polyacrylamide and C13-14 Isoparaffin and Laureth-7 |
| SEPPIC | Sepigel 501 | C13-14 Isoparaffin; Mineral Oil; Sodium Polyacrylate; Polyacrylamide; Polysorbate 85 |

-continued

| Supplier | Name | INCI Name |
|---|---|---|
| SEPPIC | Sepigel 502 | C13-14 Isoparaffin; Isostearyl Isostearate; Sodium Polyacrylate; Polyacrylamide; Polysorbate 60 |
| SEPPIC | Simulgel 600 | Acrylamide/Sodium Acryloyldimethyltaurate Copolymer; Isohexadecane; Polysorbate 80 |
| SEPPIC | Simulgel 800 | Sodium Polyacryloyldimethyl Taurate; Isohexadecane; Sorbitan Oleate |
| SEPPIC | Simulgel A | Ammonium Polyacrylate and Isohexadecane and PEG-50 Castor Oil |
| SEPPIC | Simulgel EG | Sodium Acrylate/Acryloyldimethyl Taurate Copolymer and Isohexadecane and Polysorbate 80 |
| SEPPIC | Simulgel EPG | Sodium Acrylate/Acryloyldimethyl Taurate Copolymer and Polyisobutene and Caprylyl/Capryl Glucoside |
| SEPPIC | Simulgel NS | Hydroxyethyl Acrylate/Sodium Acryloyldimethyl Taurate Copolymer and Squalane and Polysorbate 60 |
| Sud-Chemie | Pure-Thix M | PEG-180/Laureth-50/TMMG copolymer |

Particularly preferred are taurate homopolymers and copolymers. The copolymers are especially useful wherein the taurate repeating monomer unit is acryloyl dimethyl taurate (in either free acid or salt form). Monomers forming the copolymer with taurate may include: styrene, acrylic acid, methacrylic acid, vinyl chloride, vinyl acetate, vinyl pyrrolidone, isoprene, vinyl alcohol, vinyl methylether, chloro-styrene, dialkylamino-styrene, maleic acid, acrylamide, methacrylamide and mixtures thereof. Where the term "acid" appears, the term means not only the free acid but also $C_1$-$C_{30}$ alkyl esters, anhydrides and salts thereof. Preferably but not exclusively the salts may be ammonium, alkanolammonium, alkali metal and alkaline earth metal salts. Most preferred are the ammonium and alkanolammonium salts.

Most preferred as the copolymer is Acryloyl Dimethyltaurate/Vinyl Pyrrolidone Copolymer, which is the INCI nomenclature, for a material supplied by Clariant Corporation under the trademark Aristoflex® AVC, having the following general formula:

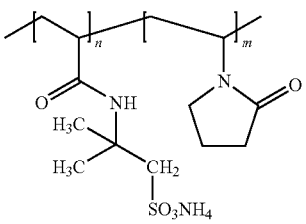

wherein n and m are integers which may independently vary from 1 to 10,000.

Number average molecular weight of copolymers according to the invention may range from about 1,000 to about 3,000,000, preferably from about 3,000 to about 100,000, optimally from about 10,000 to about 80,000.

Amounts of the associative polymer may range from about 0.001 to about 10%, preferably from about 0.01 to about 8%, more preferably from about 0.1 to about 5%, optimally from about 0.2 to about 1% by weight of the composition.

A crystalline structurant advantageously may be present in compositions according to the present invention. The structurant may include both a surfactant and a co-surfactant. The nature of the surfactant and co-surfactant will depend upon whether the crystalline structurant is anionic or nonionic. For structurants that are anionic, the preferred surfactants are $C_{10}$-$C_{22}$ fatty acids and salts (i.e. soap) thereof and particularly combinations of these materials. Typical counterions forming the fatty acid salt are those of ammonium, sodium, potassium, lithium, trialkanolammonium (e.g. triethanolammonium) and combinations thereof. Amounts of the fatty acid to the fatty acid salt when both present may range from about 100:1 to about 1:100, preferably from about 50:1 to about 1:50, and optimally from about 3:1 to about 1:3 by weight. Illustrative fatty acids include behenic acid, stearic acid, isostearic acid, myristic acid, lauric acid, linoleic acid, oleic acid, hydroxystearic acid and combinations thereof. Most preferred is stearic acid. Among the fatty acid salts the most preferred is sodium stearate.

The co-surfactant for an anionic crystalline structurant typically is a $C_{10}$-$C_{22}$ fatty alcohol, a $C_1$-$C_{200}$ ester of a $C_{10}$-$C_{22}$ fatty acid and particularly combinations of these materials. Relative amounts of the ester to the alcohol when both present may range from about 100:1 to about 1:100, preferably from about 50:1 to about 1:50, and optimally from about 3:1 to about 1:3 by weight. Typical fatty alcohols include behenyl alcohol, stearyl alcohol, cetyl alcohol, myristyl alcohol, lauryl alcohol, oleyl alcohol and combinations thereof. Esters of the fatty acid preferably are polyol esters such as $C_2$-$C_3$ alkoxylated alcohol esters. Among these are the polyethoxy, polypropoxy and block polyethyoxy/polypropoxy alcohol esters. Particularly preferred are such esters as PEG-100 stearate, PEG-20 stearate, PEG-80 laurate, PEG-20 laurate, PEG-100 palmitate, PEG-20 palmitate and combinations thereof.

The relative amount of surfactant and co-surfactant for the anionic structurant may range from about 50:1 to about 1:50, preferably from about 10:1 to about 1:10, and optimally from about 3:1 to about 1:3 by weight.

Nonionic type crystalline structurant will have a surfactant and a co-surfactant different than that for the anionic systems. Preferred nonionic structurant surfactants are $C_1$-$C_{200}$ esters of $C_{10}$-$C_{22}$ fatty acid. Esters of the fatty acid preferably are polyol esters such as $C_2$-$C_3$ alkoxylated alcohol or sorbitol esters. Among these are the polyethoxy, polypropoxy and block polyethoxy/polypropoxy alcohol esters. Particularly preferred are such esters as Polysorbate 40, Polysorbate 60, PEG-100 stearate, PEG-20 stearate, PEG-80 laurate, PEG-20 laurate, PEG-100 palmitate, PEG-20 palmitate and combinations thereof.

The co-surfactant of a nonionic structurant typically may be a combination of a $C_{10}$-$C_{22}$ fatty alcohol, glyceryl esters of a $C_{10}$-$C_{22}$ fatty acid, and a $C_{10}$-$C_{22}$ unesterified fatty acid. Relative amounts of the ester to the alcohol may range from about 100:1 to about 1:100, preferably from about 50:1 to about 1:50, and optimally from about 3:1 to about 1:3 by weight. Relative amounts of the combination of glyceryl ester and fatty alcohol to unesterified fatty acid may range from about 100:1 to about 1:100, preferably from about 50:1 to about 1:50, and optimally from about 3:1 to about 1:3 by weight. Typical fatty alcohols include behenyl alcohol, stearyl alcohol, cetyl alcohol, myristyl alcohol, lauryl alcohol, oleyl alcohol and combinations thereof.

The relative amount of surfactant and co-surfactant in a nonionic structurant may range from about 50:1 to about 1:50, preferably from about 10:1 to about 1:10, and optimally from about 3:1 to about 1:3 by weight.

A crystalline structurant is formed by the surfactant and co-surfactant. Indeed, the surfactant and co-surfactant combination in their relative ratio and type of material is defined by an enthalpy which may range from about 2 to about 15, preferably from about 2.5 to about 12, and optimally from about 3.5 to about 8 Joules per gram, as measured by Differential Scanning Calorimetry. Furthermore, the crystalline structurant system advantageously may have a melting point ranging from about 30 to about 70° C., preferably from about 45 to about 65° C., and optimally from about 50 to about 60° C.

Normal forces which are positive numbers reflect a silky smooth skin feel of the formulation. Negative values have been identified with a draggy feel which many consumers dislike. Normal force is measured in the following manner. A rheometer that has a shear rate mode capability and a normal force transducer is utilized to measure the high shear normal force. These devices are available from Rheometric Scientific ARES, TA Instruments AR2000, and Paar Physica MCR. Samples are compressed between concentric parallel plates of diameter 25 mm and gap (vertical distance between the two plates) of 100 microns. The measurements are made in a continuous logarithmic shear sweep mode with a shear rate range of 1 to 10,000 $s^{-1}$. Each sweep takes 5 minutes and is conducted at ambient condition (20-25° C.). The normal force is calculated by subtracting the baseline (defined as the normal force value at or near 100 $s^{-1}$) from the highest normal force value measured between 1000 and 10,000 $s^{-1}$. A positive normal force of 5 grams and especially 10 grams or greater is correlated to products/materials with silky sensations during rubbing in application.

The higher the positive value of the normal force the better is the soft focus effect. Ordinarily, soft focus is enhanced when the normal force ranges from about +5 to about +100 grams. Particularly desirable is a positive normal force in the range from about +10 to about +60, optimally from about +25 to about +40 grams.

A variety of other components may be present in the compositions of the present invention. Foremost is that of water which serves as a carrier in the carrier system. Amounts of water may range from about 1 to about 90%, preferably from about 30 to about 80%, optimally from about 50 to about 80% by weight of the composition.

Emollient materials may be included as carriers in compositions of this invention. These may be in the form of silicone oils, synthetic esters and hydrocarbons. Amounts of the emollients may range anywhere from about 0.1 to about 95%, preferably between about 1 and about 50% by weight of the composition.

Silicone oils may be divided into the volatile and nonvolatile variety. The term "volatile" as used herein refers to those materials which have a measurable vapor pressure at ambient temperature (20-25° C.). Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to 0.1 $m^2$/s at 25° C. Among the preferred nonvolatile emollients useful in the present compositions are the polydimethyl siloxanes having viscosities from about $1 \times 10^{-5}$ to about $4 \times 10^{-4}$ $m^2$/s at 25° C.

Among the ester emollients are:

Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

Ether-esters such as fatty acid esters of ethoxylated fatty alcohols.

Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.

Wax esters such as beeswax, spermaceti wax and tribehenin wax.

Sterols esters, of which cholesterol fatty acid esters are examples thereof.

Sugar ester of fatty acids such as sucrose polybehenate and sucrose polycottonseedate.

Hydrocarbons which are suitable cosmetically acceptable carriers include petrolatum, mineral oil, $C_{11}$-$C_{13}$ isoparaffins, polyalphaolefins, and especially isohexadecane, available commercially as Permethyl 101A from Presperse Inc.

Humectants of the polyhydric alcohol-type can be employed as cosmetically acceptable carriers. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from 0.5 to 50%, preferably between 1 and 15% by weight of the composition. Most preferred is glycerol (also known as glycerin). Amounts of glycerin may range from about 10% to about 50%, preferably from 12 to 35%, optimally from 15 to 30% by weight of the composition.

Sunscreen actives may also be included in compositions of the present invention. These will be organic compounds having at least one chromophoric group absorbing within the ultraviolet ranging from 290 to 400 nm. Chromophoric organic sunscreen agents may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, alpha-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxynaphthoic acid and its salts; o- and p-Hydroxybiphenyidisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzone, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; Etocrylene; and 4-isopropyl-dibenzoylmethane). Particularly useful are: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)]aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid and mixtures thereof.

Particularly preferred are such materials as ethylhexyl p-methoxycinnamate, available as Parsol MCX®, Avobenzene, available as Parsol 1789®, and Dermablock OS® (octylsalicylate).

Amounts of the organic sunscreen agent will range from about 0.1 to about 15%, preferably from about 0.5% to about 10%, optimally from about 1% to about 8% by weight of the composition.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Compositions of the present invention may also contain vitamins. Illustrative water-soluble vitamins are Niacinamide, Vitamin $B_2$, Vitamin $B_6$, Vitamin C and Biotin. Among the useful water-insoluble vitamins are Vitamin A (retinol), Vitamin A Palmitate, ascorbyl tetraisopalmitate, Vitamin E (tocopherol), Vitamin E Acetate and DL-panthenol. Total amount of vitamins when present in compositions according to the present invention may range from 0.001 to 10%, preferably from 0.01% to 1%, optimally from 0.1 to 0.5% by weight of the composition.

Desquamation agents are further optional components. Illustrative are the alpha-hydroxycarboxylic acids and beta-hydroxycarboxylic acids and salts of these acids. Among the former are salts of glycolic acid, lactic acid and malic acid. Salicylic acid is representative of the beta-hydroxycarboxylic acids. Amounts of these materials when present may range from about 0.1 to about 15% by weight of the composition.

A variety of herbal extracts may optionally be included in compositions of this invention. Illustrative are pomegranate, white birch (*Betula Alba*), green tea, chamomile, licorice and extract combinations thereof. The extracts may either be water soluble or water-insoluble carried in a solvent which respectively is hydrophilic or hydrophobic. Water and ethanol are the preferred extract solvents.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

Example 1

A series of formulas were investigated for their optical properties. These are recorded in Table I below.

TABLE I

| Component | INCI/Chemical Name | Sample No. (Weight %) | | | | | | | |
| --- | --- | --- | --- | --- | --- | --- | --- | --- | --- |
| | | 1 | 2 | 3 | 4 | 5 | 6 | 7 | 8 |
| Surfactant Gel | | | | | | | | | |
| Tween ® 40 | Polysorbate 40 | 1.62 | 1.62 | 1.62 | 1.62 | 1.62 | 1.62 | 1.62 | 1.62 |
| Lanette ® 16 | Cetyl Alcohol | 1.55 | 1.55 | 1.55 | 1.55 | 1.55 | 1.55 | 1.55 | 1.55 |
| Cutina ® GMS | Glycerin Monostearate | 0.78 | 0.78 | 0.78 | 0.78 | 0.78 | 0.78 | 0.78 | 0.78 |
| Emersol ® 315 | Linoleic Acid | 0.10 | 0.10 | 0.10 | 0.10 | 0.10 | 0.10 | 0.10 | 0.10 |

TABLE I-continued

| Component | INCI/Chemical Name | Sample No. (Weight %) | | | | | | | |
|---|---|---|---|---|---|---|---|---|---|
| | | 1 | 2 | 3 | 4 | 5 | 6 | 7 | 8 |
| Pristerene ® 9559 | Stearic Acid | 0.25 | 0.25 | 0.25 | 0.25 | 0.25 | 0.25 | 0.25 | 0.25 |
| Cholesterol NF | Cholesterol | 0.20 | 0.20 | 0.20 | 0.20 | 0.20 | 0.20 | 0.20 | 0.20 |
| *Humectant/emollient* | | | | | | | | | |
| Glycerin | | 9.00 | 9.00 | 9.00 | 9.00 | 9.00 | 9.00 | 9.00 | 9.00 |
| *Sunscreen* | | | | | | | | | |
| Dermablock ® OS | Ethylhexyl Salicylate | 2.00 | 2.00 | 2.00 | 2.00 | 2.00 | 2.00 | 2.00 | 2.00 |
| Parsol ® MCX | Ethylhexyl Methoxycinnamate | 4.00 | 4.00 | 4.00 | 4.00 | 4.00 | 4.00 | 4.00 | 4.00 |
| *Oil Phase* | | | | | | | | | |
| Dow Corning 200 (50 cSt) | Dimethicone | 1.00 | 1.00 | 1.00 | 1.00 | 1.00 | 1.00 | 1.00 | 1.00 |
| Dow Corning 245 | Cyclopentasiloxane | | 20.00 | | | | | | |
| Dow Corning 5225C | Formulation Aid | 0.50 | 0.50 | 0.50 | 0.50 | 0.50 | 0.50 | 0.50 | 0.50 |
| Dow Corning 9045 | Silicone Elastomer Polymer | 20.00 | | 20.00 | 20.00 | 20.00 | 20.00 | 20.00 | 20.00 |
| Aristoflex ® AVC | Taurate Copolymer | 0.80 | 0.80 | 0.80 | 0.80 | 0.80 | 0.80 | 0.40 | 0.60 |
| *Particulates* | | | | | | | | | |
| Z-Cote ® HP1 as Dispersion (65% ZnO) | Zinc Oxide | 3.08 | 3.08 | | 3.08 | 3.08 | 3.08 | 3.08 | 3.08 |
| Ganzpearl ® GMP-0820 | Polymethylmethacrylate | 0.50 | 0.50 | 0.50 | | 0.50 | 0.50 | 0.50 | 0.50 |
| Satin Mica | Mica | 0.50 | 0.50 | 0.50 | 0.50 | | 0.50 | 0.50 | 0.50 |
| Timiron ® MP 111 | TiO$_2$ Coated Mica | 1.00 | 1.00 | 1.00 | 1.00 | 1.00 | | 1.00 | 1.00 |
| Water | | 53.12 | 53.12 | 56.20 | 53.62 | 53.62 | 54.12 | 53.52 | 53.32 |

Optical Measurements

Opacity is the measure of intensity attenuation of a transmitted light beam shone perpendicular to a medium or film. The higher the direct beam attenuation, the greater will be the opacity. The source of the light beam attenuation is two fold: A) Some of the original light is reflected back from the film/medium. This gives the film/medium a true white/opaque appearance with great hiding power. Using pigment-grade TiO$_2$ in a formulation will give the effect. B) Some of the light is deflected from the straight beam path but still transmitted through the film/medium. In effect, the film/medium goes from being transparent to translucent, creating a "blurred" image. Another term for this is soft focus.

Procedure: Apply (or draw down) a 3 mil (76.2 μm) film of a formulation using a draw down bar on to a plastic overhead transparency sheet. Let the film dry for 2 hours at room temperature. Take the coated overhead transparency and place it in an Instrument Systems goniospectrophotometer. Set the light source and detector arrayed in a straight line perpendicular to the coated transparency. The light source (set at 209 million Watt-nm/cm$^2$, which serves as a reference for all Transmission Intensity values reported herein) is turned on and the measurement of the transmitted light intensity is made. Further measurements are made by moving the detector 10, 30, 40, 50 degrees away from the direct transmission normal. These values indicate the extent of soft focus light scattering. The Reflectance or "radiance" of a product is determined in the same way as opacity/soft focus light scattering, except for the positions of the light source and detector. The detector is 30 degrees on one side of the normal/perpendicular, while the light source is 20 degrees on the other side. To determine the extent of the intensity attenuation, compare the intensity value to that of an uncoated overhead transparency. The difference between these two values is the extent of the attenuation or opacity.

Results: The effect of certain components on the optical properties of the compositions was evaluated by testing formulations with those components removed. Results are reported in Table II.

TABLE II

| | Sample No. (W-nm/cm$^2$) | | | | | | | | Acceptability Transmission Intensity (Watt-nm/cm$^2$) |
|---|---|---|---|---|---|---|---|---|---|
| | 1 | 2 | 3 | 4 | 5 | 6 | 7 | 8 | |
| Transmission Angle in degrees | | | | | | | | | |
| 0 | 5.5M | 10M | 10M | 5.1M | 7.9M | 11M | 10M | 7.2M | 4 to 7 million |
| 10 | 1.1M | 1.0M | 1.6M | 1.1M | 1.2M | 1.3M | 1.1M | 1.1M | 1 to 2 million |
| 30 | 128K | 98K | 104K | 143K | 131K | 116K | 110K | 116K | 120 to 140 thousand |
| 40 | 73K | 56K | 46K | 80K | 71K | 64K | 63K | 61K | 60 to 80 thousand |
| 50 | 48K | 37K | 25K | 52K | 45K | 41K | 41K | 45K | 40 to 60 thousand |

TABLE II-continued

| | Sample No. (W-nm/cm$^2$) | | | | | | | | Acceptability Transmission Intensity (Watt-nm/cm$^2$) |
|---|---|---|---|---|---|---|---|---|---|
| | 1 | 2 | 3 | 4 | 5 | 6 | 7 | 8 | |
| Reflection Angle in degrees | | | | | | | | | |
| 30 | 154K | 160K | 195K | 160K | 131K | 109K | 160K | 155K | 140 to 170 thousand |

Note:
Bold values are outside the Acceptability range.

Sample 1 is a preferred embodiment of the present invention. Transmission Intensity (Opacity) at all angles and Reflection Intensity for this formula fell within the parameters necessary to achieve both soft focus and radiance. Replacement of the silicone elastomer (Dow Corning 9045) with cyclopentasiloxane (Dow Corning 245) in Sample 2 resulted in a Transmission Intensity at four angles outside the acceptability ranges. In Sample 3 the zinc oxide was omitted. Here the Transmission Intensity was also outside four of the acceptable ranges indicating the necessity of zinc oxide to achieve soft focus. Removal of Ganzpearl® GMP-0820, which consists of polymethylmethacrylate beads, in Sample 4 had only a small affect on the opacity. Sample 5 wherein Satin Mica was removed as expected demonstrated greater light transmission, but the Reflection Intensity and the 0° angle Transmission Intensity were outside the acceptable range. Removal of Timiron® MP 111 (titanium dioxide coated mica) in Sample 6 demonstrated that this component was a very significant contributor to the soft focus/radiance effect. In Samples 7 and 8 the amount of Aristoflex AVC® (taurate copolymer) was reduced. The 0° angle and 30° angle Transmission Intensity values were the only ones outside the acceptable range indicating that this copolymer had an influence and contributed to the soft focus effect.

Example 2

In this Example we investigated the effect of zinc oxide in contrast to titanium dioxide of essentially similar average particle sizes. Results are reported in Table IV.

TABLE III

| | | Sample No. (Weight %) | | | |
|---|---|---|---|---|---|
| Formulation # | INCI/Chemical Name | 9 | 10 | 11 | 12 |
| Surfactant Gel | | | | | |
| Tween ® 40 | Polysorbate 40 | 1.62 | 1.62 | 1.62 | 1.62 |
| Lanette ® 16 | Cetyl Alcohol | 1.55 | 1.55 | 1.55 | 1.55 |
| Cutina ® GMS | Glycerin Monostearate | 0.78 | 0.78 | 0.78 | 0.78 |
| Emersol ® 315 | Linoleic Acid | 0.10 | 0.1 | 0.1 | 0.1 |
| Pristerene ® 9559 | Stearic Acid | 0.25 | 0.25 | 0.25 | 0.25 |
| Cholesterol NF | Cholesterol | 0.20 | 0.20 | 0.20 | 0.20 |
| Humectant/Emollient | | | | | |
| Glycerin | | 9.00 | 9.00 | 9.00 | 9.00 |
| Sunscreen | | | | | |
| Dermablock ® OS | Ethylhexyl Salicylate | 2.00 | 2.00 | 2.00 | 2.00 |
| Parsol ® MCX | Ethylhexyl Methoxycinnamate | 4.00 | 4.00 | 4.00 | 4.00 |
| Oil Phase | | | | | |
| Dow Corning 200 (50 cSt) | Dimethicone | 1.00 | 1.00 | 1.00 | 1.00 |
| Dow Corning 245 | Cyclopentasiloxane | | | | |
| Dow Corning 5225C | Formulation Aid | 0.50 | 0.50 | 0.50 | 0.50 |
| Dow Corning 9040 | Silicone Elastomer | 20.00 | | | |
| Dow Corning 9045 | Silicone Elastomer | | 20.00 | 20.00 | 20.00 |
| Polymer | | | | | |
| Aristoflex ® AVC | Taurate Copolymer | 0.80 | 0.80 | 0.80 | 0.80 |
| Particulates | | | | | |
| Z-Cote ® HP1 as Dispersion (65% ZnO) | Zinc Oxide | 3.08 | | | |
| TiO$_2$ (UV-grade) | Titanium Dioxide | | 3.08 | 1.5 | 0.4 |
| Ganzpearl ® GMP-0820 | Polymethylmethacrylate | 0.50 | 0.5 | 0.5 | 0.5 |
| Satin Mica | Mica | 0.50 | 0.50 | 0.50 | 0.50 |
| Timiron ® MP 111 | Titanium Dioxide Coated Mica | 1.00 | 1.00 | 1.00 | 1.00 |
| Water | | 53.12 | 53.12 | 54.7 | 55.80 |

TABLE IV

| Sample No. | Transmission Intensity (million W-nm/cm²) at 0 degree angle |
|---|---|
| 9 | 5.1 |
| 10 | 2.3 |
| 11 | 3.5 |
| 12 | 9.0 |

On an equivalent weight basis Sample 9 provided a Transmission Intensity which was within the acceptability range. By contrast, the titanium dioxide Sample Nos. 10, 11 and 12 were outside the acceptable range.

What is claimed is:

1. A cosmetic composition comprising:
   (i) a crosslinked silicone elastomer
   (ii) a zinc oxide or zirconium oxide of average particle size from 25 to less than 100 nm;
   (iii) a light reflecting inorganic material of platelet shaped particles having an average particle size of about 10,000 to about 30,000 nm; and
   (iv) a cosmetically acceptable carrier system.

2. The composition according to claim 1 wherein the light reflecting inorganic material is titanium dioxide coated mica.

3. The composition according to claim 1 wherein the light reflecting inorganic material is bismuth oxychloride.

4. The composition according to claim 1 wherein the light reflecting inorganic material has a refractive index greater than about 1.8.

5. The composition according to claim 1 wherein the weight ratio of oxide to light reflecting inorganic material platelet shaped particles ranges from about 4:1 to about 1:1.

6. The composition according to claim 5 wherein the weight ratio is about 3:1 to about 1.5:1.

7. The composition according to claim 1 wherein a sum of the crosslinked silicone elastomer and the zinc oxide or zirconium oxide are present relative to the light reflecting inorganic material platelet shaped particles in a weight ratio from about 10:1 to about 1:1.

8. The composition according to claim 7 wherein the weight ratio ranges from about 5:1 to about 3:1.

9. The composition according to claim 1 further comprising porous particles of polymethylmethacrylate present from about 0.01 to about 10% by weight of the composition.

10. The composition according to claim 2 further comprising from about 0.05 to about 2% of a non-coated mica of average particle size ranging from 1,000 to 10,000 nm.

11. The composition according to claim 1 having a Transmission Intensity of 4 to 7 million watt-nm/cm² measured at an angle of 0°; a Transmission Intensity ranging from 1 to 2 million watt-nm/cm² measured at a 10° angle; a Transmission Intensity ranging from 120 to 140 thousand watt-nm/cm² measured at a 30° angle; a Transmission Intensity ranging from 60 to 80 thousand watt-nm/cm² measured at a 40° angle; and a Transmission Intensity ranging from 40 to 60 thousand watt-nm/cm² measured at a 50° angle.

12. A composition according to claim 11 wherein the composition has a Reflection Intensity ranging from 140 to 170 thousand watt-nm/cm² measured at a 30° angle.

13. A composition comprising:
   (i) from about 0.01 to about 30% of a crosslinked silicone elastomer by weight of the composition;
   (ii) from about 0.1 to about 20% of a zinc oxide by weight of the composition, the zinc oxide having an average particle size from 25 to less than 100 nm;
   (iii) from about 0.1 to about 5% of a light reflecting inorganic material of platelet shaped particles by weight of the composition, the particles having an average particle size of about 10,000 to about 30,000 nm; and
   (iv) a cosmetically acceptable carrier system; and
   wherein the composition has a Transmission Intensity of 4 to 7 million watt-nm/cm² measured at an angle of 0°; a Transmission Intensity ranging from 1 to 2 million watt-nm/cm² measured at a 10° angle; a Transmission Intensity ranging from 120 to 140 thousand watt-nm/cm² measured at a 30° angle; a Transmission Intensity ranging from 60 to 80 thousand watt-nm/cm² measured at a 40° angle; and a Transmission Intensity ranging from 40 to 60 thousand watt-nm/cm² measured at a 50° angle.

14. The composition according to claim 13 wherein the cosmetically acceptable carrier system comprises from about 30 to about 90% water by weight of the composition.

15. The composition according to claim 13 wherein the cosmetically acceptable carrier system comprises from about 50 to about 80% water by weight of the composition.

16. The composition according to claim 13 wherein the light reflecting inorganic material is titanium dioxide coated mica.

17. The composition according to claim 13 wherein the light reflecting inorganic material is bismuth oxychloride.

18. The composition according to claim 13 further comprising from about 0.05 to about 2% of a non-coated mica of average particle size ranging from 1,000 to 10,000 nm.

19. The composition according to claim 1 wherein the cosmetically acceptable carrier system comprises from about 30 to about 90% water by weight of the composition.

20. The composition according to claim 9 wherein the porous particles of polymethylmethacrylate have an Oil Absorbance ranging from about 90 to about 500 ml/100 grams and a density from about 0.08 to 0.55 g/cm³.

21. The composition according to claim 13 further comprising porous particles of polymethylmethacrylate present from about 0.01 to about 10% by weight of the composition.

22. The composition according to claim 1 wherein the average particle size of the zinc oxide or zirconium oxide ranges from 25 to 75 nm.

23. The composition according to claim 21 wherein the porous particles of polymethylmethacrylate have an Oil Absorbance ranging from about 90 to about 500 ml/100 grams and a density from about 0.08 to 0.55 g/cm³.

* * * * *